(12) United States Patent
Kim et al.

(10) Patent No.: US 10,196,561 B2
(45) Date of Patent: Feb. 5, 2019

(54) ELECTROCHROMIC MATERIAL AND TRANSMITTANCE VARIABLE PANEL AND DISPLAY DEVICE INCLUDING THE SAME

(71) Applicant: LG Display Co., Ltd., Seoul (KR)

(72) Inventors: June-Hwan Kim, Paju-si (KR);
Soo-Youn Kim, Paju-si (KR);
Seong-Yong Uhm, Paju-si (KR);
Young-Wook Ha, Paju-si (KR);
Hark-Jin Kim, Paju-si (KR)

(73) Assignee: LG Display Co., Ltd., Seoul (KR)

( * ) Notice: Subject to any disclaimer, the term of this patent is extended or adjusted under 35 U.S.C. 154(b) by 13 days.

(21) Appl. No.: 15/623,007

(22) Filed: Jun. 14, 2017

(65) Prior Publication Data

US 2017/0369771 A1    Dec. 28, 2017

(30) Foreign Application Priority Data

Jun. 24, 2016    (KR) ........................ 10-2016-0079448

(51) Int. Cl.
*G02F 1/15* (2006.01)
*C09K 9/02* (2006.01)
*C07F 9/6558* (2006.01)

(52) U.S. Cl.
CPC ............ *C09K 9/02* (2013.01); *C07F 9/65583* (2013.01); *G02F 1/15* (2013.01); *C09K 2211/1007* (2013.01); *C09K 2211/1014* (2013.01); *C09K 2211/1022* (2013.01); *G02F 2001/1502* (2013.01); *G02F 2001/1515* (2013.01)

(58) Field of Classification Search
CPC .................................... C09K 9/02; G02F 1/15
See application file for complete search history.

(56) References Cited

U.S. PATENT DOCUMENTS

2002/0015214 A1* 2/2002 Nishikitani ............. C09K 9/02
                                                              359/265
2011/0002027 A1    1/2011 Das et al.

FOREIGN PATENT DOCUMENTS

| CN | 1738885 A | 2/2006 |
| JP | 2015-124228 A | 7/2015 |
| KR | 10-2011-0002750 A | 1/2011 |
| KR | 101535100 B1 | 7/2015 |
| KR | 10-2015-0144455 A | 12/2015 |
| WO | 2015/193301 A1 | 12/2015 |

OTHER PUBLICATIONS

Murugavel., "Benzylic viologen dendrimers: a review of their synthesis, properties and applications," *Polym. Chem.* 5:5873-5884, 2014.
Chinese Office Action dated Nov. 27, 2018 for Chinese Application No. 201710485758.2, 20 pages. (With English Translation).

* cited by examiner

*Primary Examiner* — Joseph P Martinez
(74) *Attorney, Agent, or Firm* — Seed IP Law Group LLP

(57) ABSTRACT

The present disclosure relates to an electrochromic material having a relatively high response speed and a reversible discoloration even by a relatively low driving voltage and an electrochromic particle, a transmittance variable panel and a transmittance variable display device including the electrochromic material.

11 Claims, 7 Drawing Sheets

ELECTROCHROMIC MATERIAL AND TRANSMITTANCE VARIABLE PANEL AND DISPLAY DEVICE INCLUDING THE SAME

CROSS-REFERENCE TO RELATED APPLICATIONS

This application claims the benefit under 35 U.S.C. § 119(a) of Korean Patent Application No. 10-2016-0079448, filed on Jun. 24, 2016, in the Korean Intellectual Property Office, which is incorporated herein by reference in its entirety.

BACKGROUND

Technical Field

The present disclosure relates to an electrochromic material for a display device, and more particularly, to an electrochromic material having an excellent transmittance and an excellent blocking degree, and an electrochromic particle, a transmittance variable panel and a display device including the electrochromic material.

Description of the Related Art

As an information society progresses, a request for a flat panel display of an excellent image increases. Among various flat panel displays, a liquid crystal display (LCD) device and an organic light emitting diode (OLED) display device have been the subject of recent research.

The LCD device displays an image using an optical anisotropy and a polar property of a liquid crystal molecule. For example, the LCD device may include a first substrate having a pixel electrode and a common electrode, a second substrate facing the first substrate and a liquid crystal layer including the liquid crystal molecule between the first and second substrates. The OLED display device displays an image using an emission of an emitting layer. For example, the OLED display device may include an anode, a cathode facing the anode and an emitting layer between the anode and the cathode. A hole injected from the anode and an electron injected from the cathode are combined to form an exciton, and the exciton transitions from an excited state to a ground state to emit a light.

Recently, a transparent display device a whole of which is transparent has been suggested. Specifically, the transparent display device may be used as a window type display device such as a smart window. However, since the transparent display device does not have a black state, a contrast ratio and a visibility of the transparent are reduced.

To improve the above disadvantages, a blocking plate where a transmittance is changed according to a discoloration of a particle or a movement of a particle has been suggested. For example, a transmittance variable panel such as a liquid crystal panel, an electrophoretic panel, an electrowetting panel and an electrochromic panel having a variable transmittance may be used as the blocking plate.

When the liquid crystal panel is used as the transmittance variable panel, the transmittance of a transmissive mode is reduced due to the liquid crystal layer. In addition, when a color filter layer is used for various colors, a brightness is reduced. Further, since a blocking efficiency is relatively low, a contrast ratio is reduced.

The electrophoretic panel uses an electrophoresis where charged particles move according to application of a voltage. For example, black charged particles may move onto a transparent electrode to block a light when a voltage is applied, and white charged particles may move onto the transparent electrode to transmit or reflect a light when an opposite voltage is applied. As a result, the electrophoretic panel may have a blocking mode when the voltage is applied and may have a transmissive mode when the opposite voltage is applied. However, it is difficult to uniformly disperse black and/or white electrophoretic particles in an electrolyte layer. In addition, when a fluid is used for the electrolyte layer where the electrophoretic particles move, the electrophoretic particles may leak to an exterior.

When the electrowetting panel is used as the transmittance variable panel, it is difficult to fabricate the transmittance variable panel using a black oil. In addition, an extraction of a black dye or a black pigment and a leakage of a fluid such as an oil for displaying a color may occur.

The electrochromic panel uses an electrochromic material whose color is reversibly changed by an oxidation-reduction reaction according to an applied voltage. For example, an electrochromic smart window where tungsten oxide ($WO_3$), molybdenum oxide ($MoO_3$), neodymium oxide ($Nb_2O_5$), titanium oxide ($TiO_2$) or tantalum oxide ($Ta_2O_5$) is used as an electrochromic material is suggested in Korean Patent No. 10-1535100. However, the inorganic electrochromic material has a relatively low response speed and requires a relatively high driving voltage for color variation. In addition, when the inorganic electrochromic material is applied to a window type display device or a vehicle type display device, an additional infrared (IR) cut film is required because the inorganic electrochromic material can not block an infrared ray.

BRIEF SUMMARY

Embodiments relate to an electrochromic material having a relatively high transmittance and an electrochromic particle, a transmittance variable panel and a transmittance variable display device including the electrochromic material.

One or more embodiments relate to an electrochromic material having a relatively high response speed and a reversible discoloration even by a relatively low driving voltage and an electrochromic particle, a transmittance variable panel and a transmittance variable display device including the electrochromic material.

One or more embodiments relate to an electrochromic material having an excellent effect of blocking an infrared ray and an electrochromic particle, a transmittance variable panel and a transmittance variable display device including the electrochromic material.

Advantages and features of the disclosure will be set forth in part in the description, which follows and in part will become apparent to those having ordinary skill in the art upon examination of the following or may be learned from practice of the disclosure. Other advantages and features of the embodiments herein may be realized and attained by the structure particularly pointed out in the written description and claims hereof as well as the appended drawings.

It is to be understood that both the foregoing general description and the following detailed description are explanatory, and are intended to provide further explanation of the embodiments as claimed.

BRIEF DESCRIPTION OF THE DRAWINGS

The accompanying drawings, which are included to provide a further understanding of the disclosure, are incorporated in and constitute a part of this specification, illustrate implementations of the disclosure and together with the description serve to explain the principles of embodiments of the disclosure.

DETAILED DESCRIPTION

Figure 1:
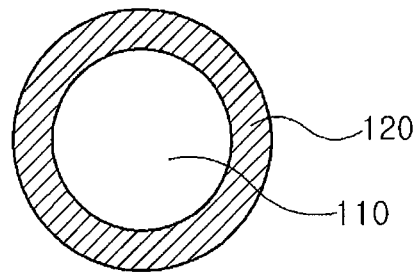
FIG. 1 is a view showing an electrochromic particle of a core-shell structure having a single core according to a first embodiment of the present disclosure.

Reference will now be made in detail to embodiments of the present disclosure, examples of which are illustrated in the accompanying drawings. In the following description, when a detailed description of well-known functions or configurations related to this document is determined to unnecessarily cloud a gist of an embodiment of the disclosure, the detailed description thereof will be omitted. The progression of processing steps and/or operations described is an example; however, the sequence of steps and/or operations is not limited to that set forth herein and may be changed as is known in the art, with the exception of steps and/or operations necessarily occurring in a certain order. Like reference numerals designate like elements throughout. Names of the respective elements used in the following explanations are selected only for convenience of writing the specification and may be thus different from those used in actual products.

The present disclosure provides an electrochromic material represented by a following chemical formula 1.

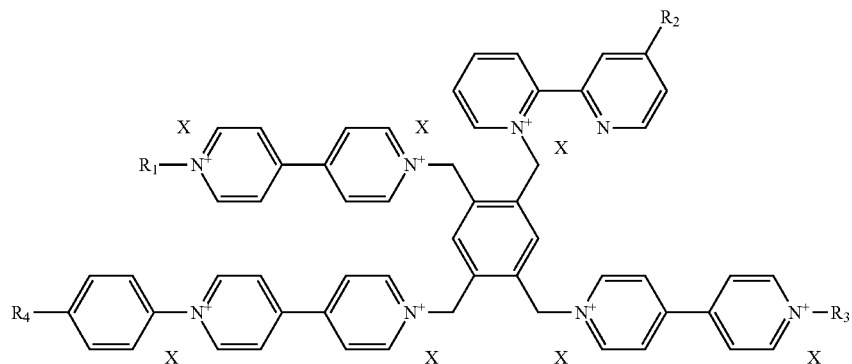

Chemical Formula 1

In the chemical formula 1, R1 is selected from a group including a hydrogen atom, an alkyl group of C1 to C30, an alkenyl of C2 to C30, an alkynyl group of C2 to C30, an alkoxy group of C1 to C30, a cycloalkyl group of C4 to C30, a heterocycloalkyl group of C4 to C30, an aryl group of C5 to C30, a heteroaryl group of C5 to C30, an aralkyl group of C5 to C30, an heteroaralkyl group of C5 to C30, an aryloxy group of C5 to C30 and an heteroaryloxy group of C5 to C30; each of R2 and R3 is —W—Z, wherein Z is independently selected from a group including a carboxylic acid (—COOH), a sulfonic acid (—SO$_3$H$_2$), a boronic acid (B(OH)$_2$), a phosphoric acid (PO$_3$H$_2$) and a phosphinic acid (PO$_2$H$_2$), and W is a direct bond or an alkylene group of C1 to C20; R4 is an alkyl group of C1 to C10 substituted by one or more halogens or an alkoxy group of C1 to C10 substituted by one or more halogens; X is a halogen negative ion, PF$_6^-$, BF$_4^-$, BH$_4^-$, ClO$_4^-$, CF$_3$SO$_3^-$ or (CF$_3$SO$_2$)$_2$N$^-$. As used herein, "alkylene" refers to a diradical of a hydrocarbon chain of C1 to C20 that links the Z group to the remainder of the molecule. Halogen refers to fluoro, chloro, bromo or iodo group. Halogen negative ion refers to fluoride (F), chloride (Cl$^-$), bromide (Br$^-$) or iodide (I$^-$).

For example, the electrochromic material may include one of compounds represented by following chemical formulas 2 to 5.

Chemical Formula 2
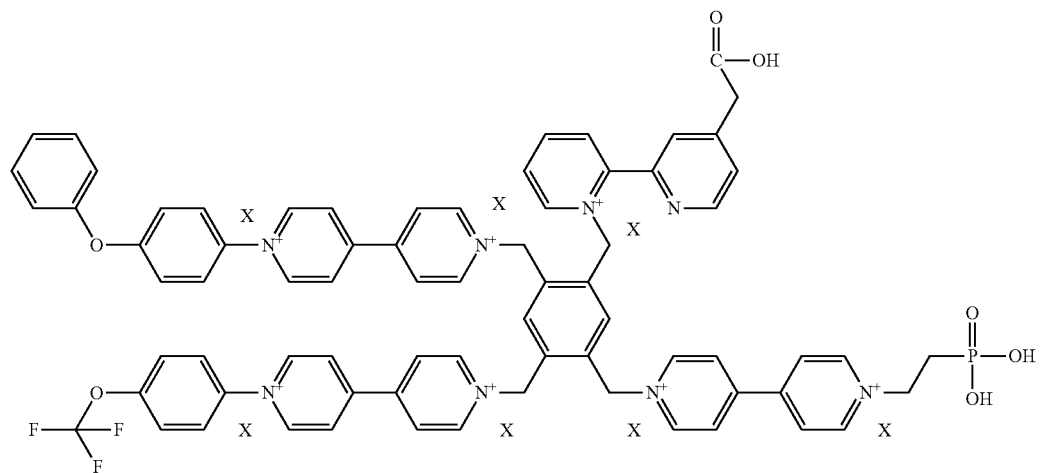
Chemical Formula 3
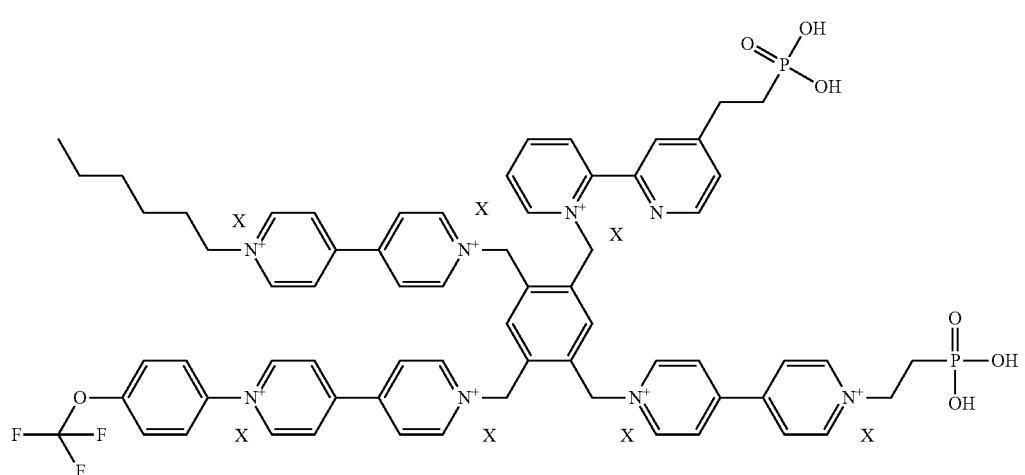
Chemical Formula 4
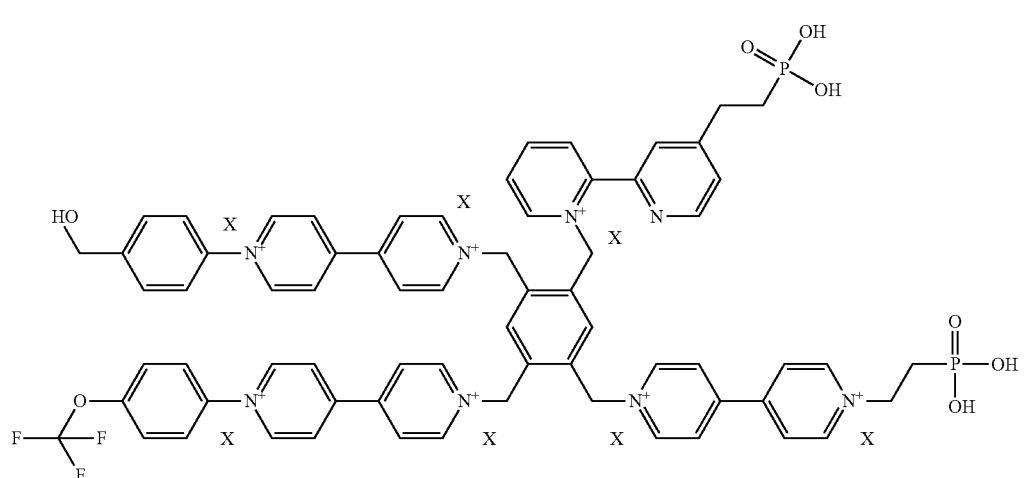

-continued

Chemical Formula 5

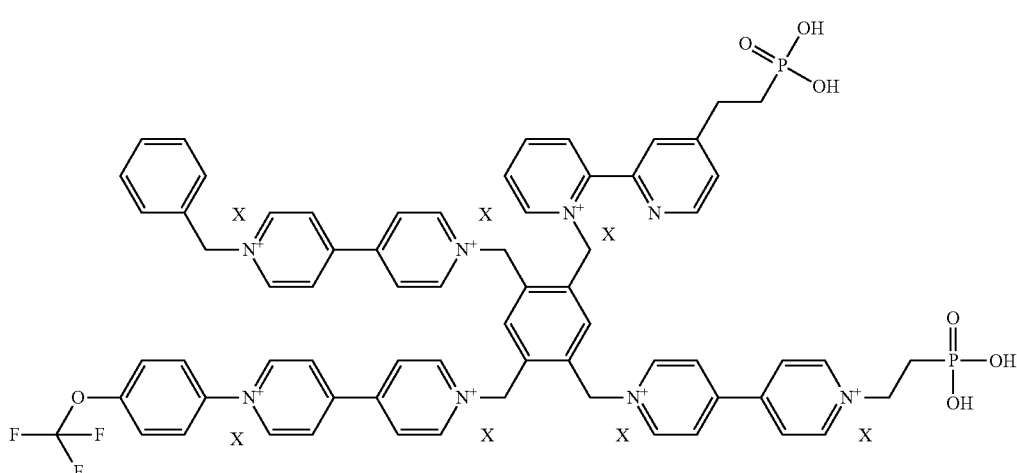

In the chemical formulas 2 to 5, a definition of X is the same as that in the chemical formula 1.

In another aspect, the present disclosure provides an electrochromic particle including a core and a shell where the shell includes an electrochromic material represented by the chemical formulas 1 to 5.

In an exemplary embodiment, the core may be selected from a group including a conductive metal oxide, a non-conductive metal oxide and a combination thereof. The conductive metal oxide may be selected from a group including indium tin oxide (ITO), indium zinc oxide (IZO), antimony tin oxide (ATO), fluorine-doped tin oxide (FTO), aluminum zinc oxide (AZO) and a combination thereof, and the non-conductive metal oxide may be selected from a group including titanium oxide ($TiO_2$), silica ($SiO_2$), zinc oxide (ZnO), zirconia ($ZrO_2$) and a combination thereof.

In another exemplary embodiment, the core may include a first core and a second core wrapping the first core. The first core may include the conductive metal oxide selected from a group including indium tin oxide (ITO), indium zinc oxide (IZO), antimony tin oxide (ATO), fluorine-doped tin oxide (FTO), aluminum zinc oxide (AZO) and a combination thereof, and the second core may include the non-conductive metal oxide selected from a group including titanium oxide ($TiO_2$), silica ($SiO_2$), zinc oxide (ZnO), zirconia ($ZrO_2$) and a combination thereof.

In another aspect, the present disclosure provides a transmittance variable panel which includes first and second substrates facing each other, a first transparent electrode on an inner surface of the first substrate, a second transparent electrode on an inner surface of the second substrate and an electrochromic layer between the first and second transparent electrodes. The electrochromic layer includes the electrochromic particle.

The transmittance variable panel may further include a counter layer between the second transparent electrode and the electrochromic layer, and the counter layer may accelerate an oxidation-reduction reaction in the electrochromic layer.

In another aspect, the present disclosure provides a display device including the transmittance variable panel and a display panel adjacent to the transmittance variable panel, and the display panel includes a display portion and a transparent portion.

Electrochromic Material and Electrochromic Particle

An electrochromic material of the present disclosure may be represented by a following chemical formula 1.

Chemical Formula 1

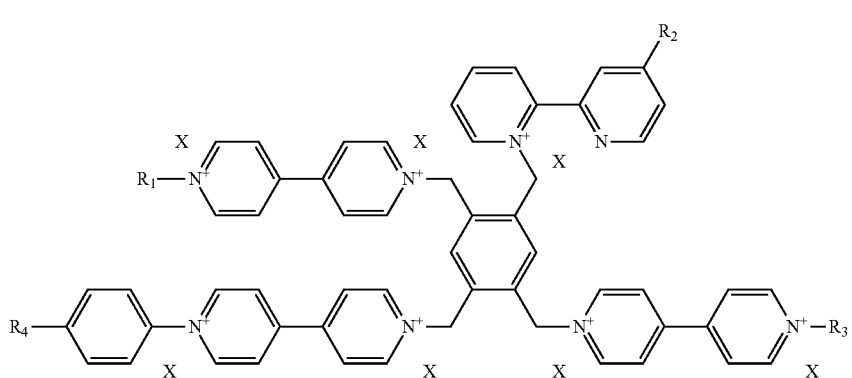

In the chemical formula 1, $R_1$ is selected from a group consisting of a hydrogen atom, an alkyl group of C1 to C30, an alkenyl of C2 to C30, an alkynyl group of C2 to C30, an alkoxy group of C1 to C30, a cycloalkyl group of C4 to C30, a heterocycloalkyl group of C4 to C30, an aryl group of C5 to C30, a heteroaryl group of C5 to C30, an aralkyl group of C5 to C30, an heteroaralkyl group of C5 to C30, an aryloxy group of C5 to C30 and an heteroaryloxy group of C5 to C30; each of R2 and R3 is —W—Z, wherein Z is independently selected from a group consisting of a carboxylic acid (—COOH), a sulfonic acid (—SO$_3$H$_2$), a boronic acid (B(OH)$_2$), a phosphoric acid (PO$_3$H$_2$) and a phosphinic acid (PO$_2$H$_2$), and W is a direct bond or an alkylene group of C1 to C20; R4 is an alkyl group of C1 to C10 substituted by one or more halogens or R4 is an alkoxy group of C1 to C10 substituted by one or more halogens; X is a halogen negative ion, PF$_6^-$, BF$_4^-$, BH$_4^-$, ClO$_4^-$, CF$_3$SO$_3^-$ or (CF$_3$SO$_2$)$_2$N$^-$.

For example, the heterocycloalkyl group, the heteroaryl group, the heteroaralkyl group and the heteroaryloxy group defined in the chemical formula 1 may be a functional group where at least one of carbon atoms constituting a ring is substituted by nitrogen (N), oxygen (O), sulfur (S) and/or phosphorus (P). In addition, any one of the cycloalkyl group, the aryl group, the aralkyl group, the aryloxy group, the heterocycloalkyl group, the heteroaryl group, the heteroaralkyl group and the heteroaryloxy group defined in the chemical formula 1 may be unsubstituted or may be substituted by a substituent selected from a group consisting of an alkyl group of C1 to C30, an alkenyl of C2 to C30, an alkynyl group of C2 to C30, an alkoxy group of C1 to C30 (i.e., a hydroxy group where a hydrogen is substituted by an alkyl group of C1 to C30), a cycloalkyl group of C4 to C30, a heterocycloalkyl group of C4 to C30, an aryl group of C5 to C30, a heteroaryl group of C5 to C30, an aralkyl group of C5 to C30, an heteroaralkyl group of C5 to C30, an aryloxy group of C5 to C30 and an heteroaryloxy group of C5 to C30. Furthermore, the alkyl group, alkenyl group, alkynyl group, alkoxy group, cycloalkyl group may be optionally substituted by halogen or hydroxy, in addition to any of the above substituents.

In an exemplary embodiment, R1 defined in the chemical formula 1 may be selected from a group including an alkyl group of C1 to C30, preferably C1 to C20, further preferably C1 to C10, which may optionally be substituted by a hydroxy; a (hetero)aryl group (i.e., an aryl or heteroaryl group) of C5 to C30, preferably C5 to C20; a (hetero)aralkyl group (i.e., an aralkyl or heteroaralkyl group) of C5 to C30, preferably C5 to C20; and a (hetero)aryloxy group (i.e., an aryloxy or heteroaryloxy group) of C5 to C30, preferably C5 to C20. In addition, each of R2 and R3 defined in the chemical formula 1 may be a carboxylic acid, a phosphoric acid or a phosphinic acid connected to an alkyl group of C1 to C20, preferably C1 to C10. R 4 defined in the chemical formula 1 may be an alkyl group or an alkoxy group of C1 to C10, preferably C1 to C5 alkyl substituted by one or more halogens (e.g., one or more fluoro), or C1 to C5 alkoxy group substituted by one or more halogens (e.g., one or more fluoro), and X defined in the chemical formula 1 may be a halogen negative ion selected from a group including a chloride ion (Cl$^-$), bromide ion (Br$^-$) and iodide ion (I$^-$), CF$_3$SO$_3^-$ or (CF$_3$SO$_2$)$_2$N$^-$.

The electrochromic material of the present disclosure may have a structure such that four linkers of a first bipyridinium salt moiety where a hydrogen atom is substituted by R1, a second bipyridinium salt moiety where a hydrogen atom is substituted by R2, a third bipyridinium salt moiety where a hydrogen atom is substituted by R3 and a fourth bipyridinium salt moiety where a hydrogen atom is substituted by a phenyl group or a phenoxy group where a hydrogen atom is substituted by R4 including a halogen are combined to a benzene ring. Specifically, since the phenyl moiety or the phenoxy moiety where a hydrogen is substituted by an electron-rich halogen for R4 and the plurality of bipyridinium salt moieties induce a stacking effect, the electrochromic material may have discoloration even with a relatively low driving voltage.

The electrochromic material forms a shell wrapping a core in an electrochromic particle of a core-shell structure, and the electrochromic particle may have an excellent transmittance property, an excellent response speed property and an excellent discoloration property even with a relatively low driving voltage. Specifically, since an inorganic functional group or an organic functional group constituting R2 and R3 in the electrochromic material of the chemical formula 1 is chemically combined with the core, a driving stability of a transmittance variable panel including the electrochromic particle of a core-shell type may be improved.

In an exemplary embodiment, the electrochromic material represented by the chemical formula 1 includes one of electrochromic materials represented by following chemical formulas 2 to 5.

Chemical Formula 2

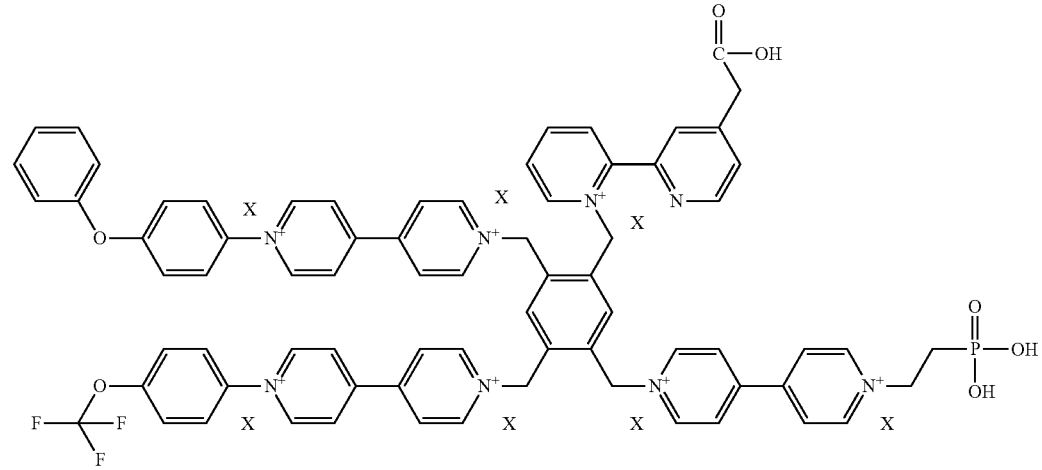

-continued

Chemical Formula 3

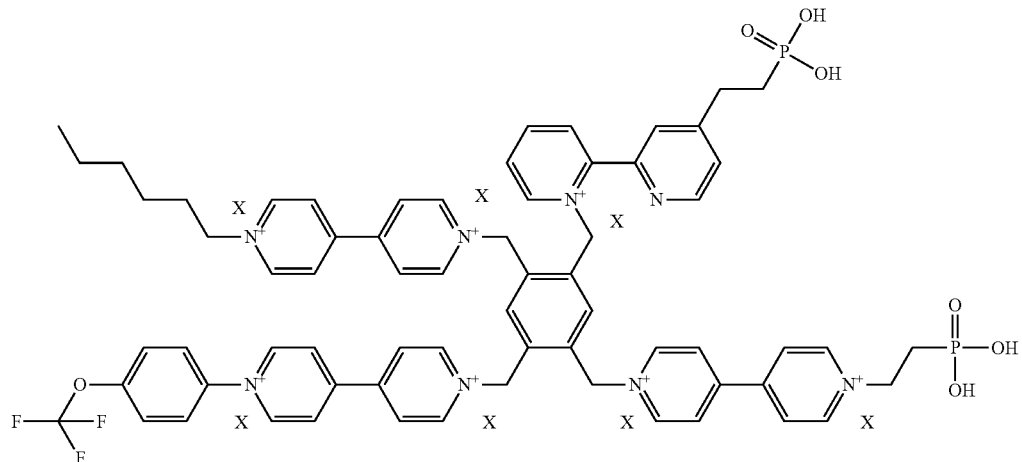

Chemical Formula 4

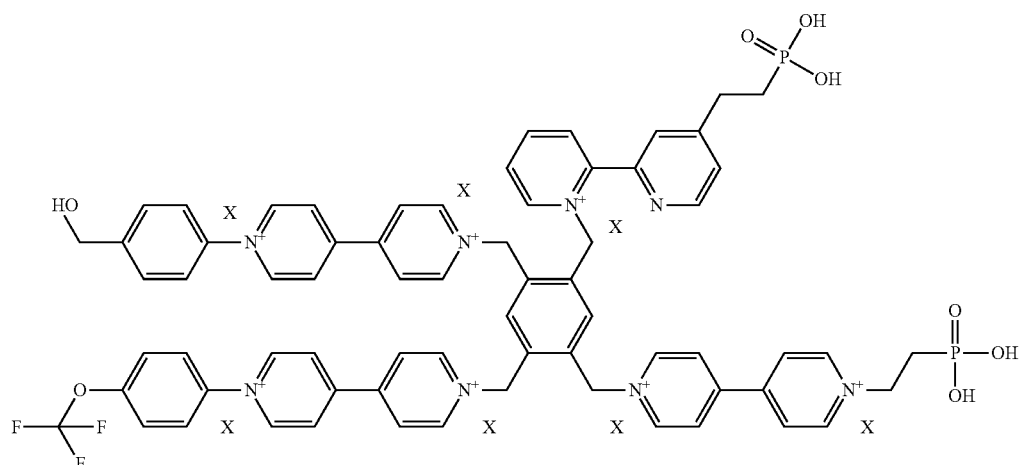

Chemical Formula 5

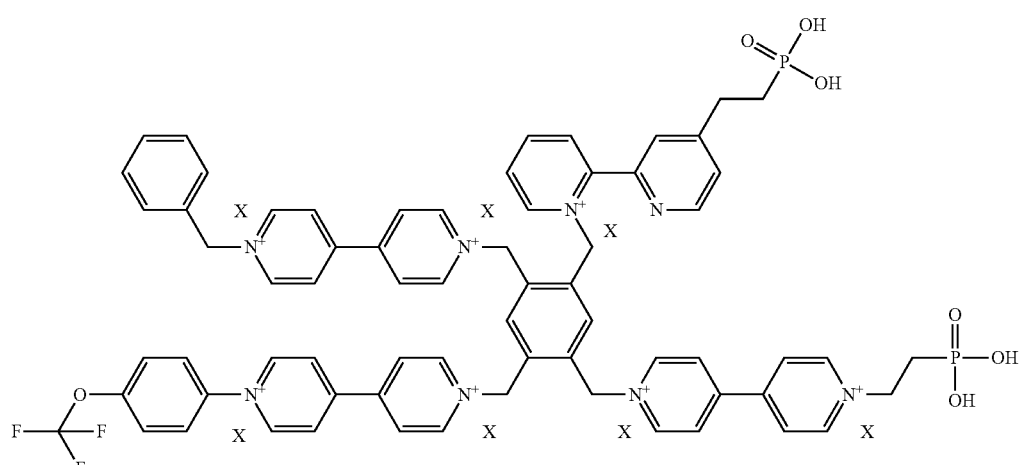

(In the chemical formulas 2 to 5, a definition of X is the same as that in the chemical formula 1.)

The electrochromic material represented by the chemical formulas 2 to 5 includes a phenoxy moiety where a hydrogen is substituted by an electron-rich trifluoromethyl group, and the phenoxy moiety induces a stacking effect with four bipyridinium salt moieties. As a result, the electrochromic material has a discoloration even with a relatively low driving voltage and a prompt discoloration due to an improved response speed. The electrochromic material forms the shell of the electrochromic particle of a core-shell type, and the electrochromic particle has an excellent transmittance property and an excellent response speed. In addition, a functional group of a carboxyl acid or a phosphoric acid is chemically combined with the core, and a driving stability of a transmittance variable panel including the electrochromic particle is improved. Further, the electrochromic material has an excellent effect of blocking an infrared ray. Accordingly, when the transmittance variable panel is applied to a smart window for a building or a vehicle, an additional infrared (IR) cut film is omitted.

The electrochromic particle including the shell of the electrochromic material of the present disclosure may be illustrated hereinafter.

FIG. 1 is a view showing an electrochromic particle of a core-shell structure having a single core according to a first embodiment of the present disclosure.

In FIG. 1, an electrochromic particle 100A according to a first embodiment of the present disclosure includes a core 110 and a shell 120 wrapping the core 110.

The core 110 may include a conductive metal oxide having an excellent transmittance with respect to a visible ray, a non-conductive metal oxide having an excellent specific surface area and a combination thereof. For example, the conductive metal oxide may include a nanoparticle of a metal oxide having an average diameter of about 30 nm to about 200 nm. The conductive metal oxide may be selected from a group including indium tin oxide (ITO), indium zinc oxide (IZO), antimony tin oxide (ATO), fluorine-doped tin oxide (FTO), aluminum zinc oxide (AZO) and a combination thereof.

For example, the non-conductive metal oxide may include a nanoparticle of a non-conductive metal oxide having a specific surface area greater than about 100 m$^2$/g and an average diameter of about 10 nm to about 100 nm. The non-conductive metal oxide may be selected from a group including titanium oxide ($TiO_2$), silica ($SiO_2$), zinc oxide (ZnO), zirconia ($ZrO_2$) and a combination thereof.

The core 110 may not be limited to the above materials. An organic material, an inorganic material or an organic-inorganic hybrid material having a relatively high transmittance with respect to a visible ray and an excellent electric conductivity and/or a non-conductive organic material, an inorganic material or an organic-inorganic hybrid material having a relatively large specific surface area may be used for the core 110.

The shell 120 may include an electrochromic material represented by the chemical formulas 1 to 5. In the electrochromic material of the chemical formulas 1 to 5, a plurality of bipyridinium salt moieties are combined to a benzene ring, and a phenyl moiety or a phenoxy moiety where a hydrogen atom is substituted by an electron-rich halogen may induce a stacking effect with the plurality of bipyridinium salt moieties. Since the electrochromic particle 100 of a structure where the electrochromic material wraps the core 110 has an excellent transparency, a transmittance increases when an electric field is not applied. Since the shell 120 of the electrochromic material is discolored into a black even by a relatively low driving voltage, a light blocking efficiency is improved. In addition, since the electrochromic material of the present disclosure is discolored into a black by application of a voltage, the electrochromic material has an excellent light blocking efficiency without mixing of other materials.

For example, since the electrochromic particle of the present disclosure is a nanoparticle having a core-shell structure of a spherical shape, a specific surface area of the electrochromic particle increases as compared with a plate shape. As a result, a response speed with respect to application of an electric field is improved, and the discoloration reaction may occur even by a relatively low driving voltage. Further, since the electrochromic material represented by the chemical formulas 1 to 5 is chemically combined, a driving stability may be improved.

Figure 2:
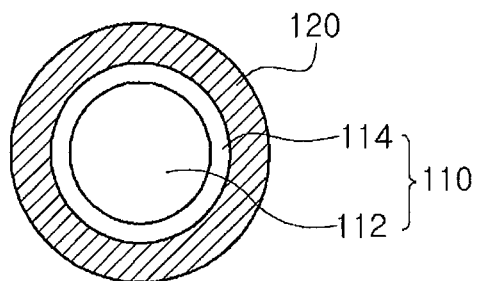
FIG. 2 is a view showing an electrochromic particle of a core-shell structure having two cores according to a second embodiment of the present disclosure.

FIG. 2 is a view showing an electrochromic particle of a core-shell structure having two cores according to a second embodiment of the present disclosure.

In FIG. 2, an electrochromic particle 100B according to a second embodiment of the present disclosure includes a core 110 having first and second cores 112 and 114 and a shell 120 wrapping the core 110.

For example, the first core 112 may include a conductive metal oxide having an excellent transmittance with respect to a visible ray and an excellent electron mobility. The first core 112 may include a nanoparticle of a conductive metal oxide having an average diameter of about 30 nm to about 200 nm. The conductive metal oxide for the first core 112 may be selected from a group including indium tin oxide (ITO), indium zinc oxide (IZO), antimony tin oxide (ATO), fluorine-doped tin oxide (FTO), aluminum zinc oxide (AZO) and a combination thereof.

The first core 112 may not be limited to the above materials. An organic material, an inorganic material or an organic-inorganic hybrid material having a relatively high transmittance with respect to a visible ray and an excellent electric conductivity may be used for the first core 112.

The second core 114 wrapping the first core 112 may include a non-conductive metal oxide having a relatively great specific surface area and a relatively high transmittance with respect to a visible ray. For example, the second core 114 may include a nanoparticle of a non-conductive metal oxide having a specific surface area greater than about 100 m$^2$/g and an average diameter of about 10 nm to about 100 nm. The non-conductive metal oxide for the second core 114 may be selected from a group including titanium oxide ($TiO_2$), silica ($SiO_2$), zinc oxide (ZnO), zirconia ($ZrO_2$) and a combination thereof.

The second core 114 may not be limited to the above materials. An organic material, an inorganic material or an organic-inorganic hybrid material having a relatively large specific surface area may be used for the second core 114.

When the core 110 of the electrochromic particle 100B has a dual core of the conductive first core 112 and the non-conductive second core 114 having a relatively great specific surface area, a transparency and a light blocking degree are improved and a low power consumption is obtained.

Since the first core 112 includes indium tin oxide (ITO) having an excellent electron moving property, an electron mobility toward the shell 120 increases in an ON state, and the shell 120 of the electrochromic material of the chemical formulas 1 to 5 is easily discolored. Since the second core 114 includes titanium oxide ($TiO_2$) having a relatively high transmittance with respect to a visible ray, a relatively high transmittance is obtained in an OFF state. In addition, since the non-conductive metal oxide of the second core 114 has the relatively great specific surface area, the second core 114 has a combination state with the shell 120, and a bistability is improved. As a result, a power consumption for driving the electrochromic particle 100B is reduced. Since a light blocking state is kept for the time being due to a relatively high bistability even when application of a voltage is stopped, a power consumption is reduced.

The shell 120 may include an electrochromic material represented by the chemical formulas 1 to 5. In the electrochromic material of the chemical formulas 1 to 5, a plurality of bipyridinium salt moieties are combined to a benzene ring, and a phenyl moiety or a phenoxy moiety where a hydrogen atom is substituted by an electron-rich halogen may induce a stacking effect with the plurality of bipyridinium salt moieties. Since the electrochromic particle 100 of a structure where the electrochromic material wraps the core 110 has an excellent transparency, a transmittance increases when an electric field is not applied. Since the shell 120 of the electrochromic material is discolored into a black even by a relatively low driving voltage, a light blocking efficiency is improved. In addition, since the electrochromic material of the present disclosure is discolored into a black by application of a voltage, the electrochromic material has an excellent light blocking efficiency without mixing of other materials.

For example, since the electrochromic particle of the present disclosure is a nanoparticle having a core-shell structure of a spherical shape, a specific surface area of the electrochromic particle increases as compared with a plate shape. Specifically, since the non-conductive metal oxide having a relatively great specific surface area is used for the second core 114 wrapping the first core 112, the specific surface area increases. As a result, a response speed with respect to application of an electric field is improved, and the discoloration reaction may occur even by a relatively low driving voltage. Further, since the electrochromic material represented by the chemical formulas 1 to 5 is chemically combined, a driving stability may be improved.

Moreover, the electrochromic material for the shell 120 has an excellent light blocking effect. As a result, when the transmittance variable panel is applied to a smart window for a building or a vehicle, an additional infrared (IR) cut film is not required.

Transmittance Variable Panel and Display Device

A transmittance variable panel and a display device of the present disclosure include an electrochromic particle of a core-shell structure where a shell wrapping a core includes an electrochromic material of the chemical formulas 1 to 5

Figure 3:
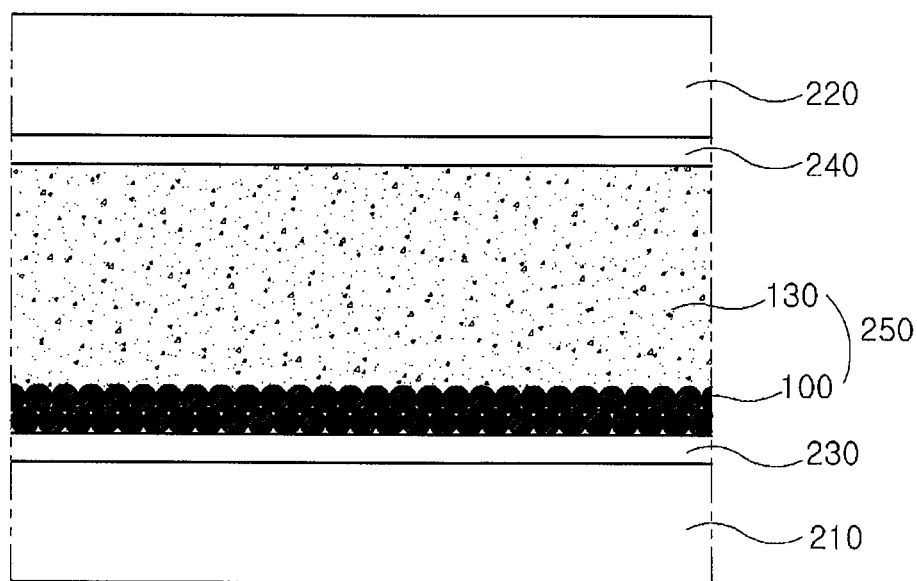
FIG. 3 is a cross-sectional view showing a transmittance variable panel according to first and second embodiments of the present disclosure.

FIG. 3 is a cross-sectional view showing a transmittance variable panel according to first and second embodiments of the present disclosure.

In FIG. 3, a transmittance variable panel 200 according to first and second embodiments of the present disclosure includes first and second substrates 210 and 220 facing into each other, a first transparent electrode 230 on an inner surface of the first substrate 210, a second transparent electrode 240 on an inner surface of the second substrate 220 and an electrochromic layer 250 having an electrochromic particle 100 and a electrolyte 130 between the first and second substrates 210 and 220.

The first and second substrates 210 and 220 may include a glass or a plastic. For example, each of the first and second substrates 210 and 220 may include polyethylene terephthalate (PET) or polyethylene naphthalate (PEN).

The first and second transparent electrodes 230 and 240 may include a transparent conductive material. For example, each of the first and second transparent electrodes 230 and 240 may include indium tin oxide (ITO) or indium zinc oxide (IZO). For increasing a transmittance of the transmittance variable panel of the present disclosure in a transmissive mode, the first and second transparent electrodes 230 and 240 may include the transparent conductive material. Alternatively, when a relatively low resistance metallic material such as aluminum (Al), copper (Cu), palladium (Pd) and a combination thereof is used for the first and second transparent electrodes 230 and 240, the first and second transparent electrodes 230 and 240 may have a relatively small thickness to transmit a light.

If necessary, the first and second transparent electrodes 230 and 240 may have a double-layered structure where a transparent conductive material such as indium tin oxide (ITO) or indium zinc oxide (IZO) is formed on a relatively low resistance metallic material such as aluminum (Al), copper (Cu), palladium (Pd) and a combination thereof. The relatively low resistance metallic material may have a mesh shape. When the transparent conductive material is formed on the metallic material of the mesh shape for the first and second transparent electrodes 230 and 240, a response speed of the electrochromic particle 100 is greatly improved, and a prompt discoloration according to application of a power is obtained.

The electrochromic layer 250 is disposed between the first and second substrates 210 and 220, i.e., between the first and second transparent electrodes 230 and 240. The electrochromic layer 250 includes the electrochromic particle 100 and the electrolyte 130. As shown in FIGS. 1 and 2, the electrochromic particle 100 has a core-shell structure where the electrochromic material of the chemical formulas 1 to 5 wraps the core. The electrochromic material of the chemical formulas 1 to 5 induces a stacking effect by the plurality of bipyridinium salt moieties and the phenyl moiety or the phenoxy moiety where a hydrogen atom is substituted by the electron-rich halogen. As a result, the electrochromic particle 100 has an excellent transmittance when a voltage is not applied. In addition, since the electrochromic particle 100 is a nanoparticle of a spherical shape having a relatively great specific surface area, the electrochromic particle 100 has a prompt discoloration even with a relatively low driving voltage. As a result, when the voltage is applied, the electrochromic particle 100 is promptly discolored to a black to have an excellent light blocking efficiency. The electrochromic material of the chemical formulas 1 to 5 has an excellent infrared (IR) cut effect. Accordingly, when the transmittance variable panel 200 is applied to a smart window for a building or a vehicle, an additional infrared (IR) cut film is not required.

The electrochromic layer 250 includes the electrolyte 130 as well as the electrochromic particle 100. For example, the electrolyte 130 may has a solid phase. When the electrolyte 130 has a liquid phase, the electrolyte 130 of a fluid may be leaked. For example, a gel type electrolyte or a polymer type electrolyte including a dissolved lithium salt may be used for the electrolyte 130. The medium of the electrolyte 130 may be cured by a heat or a light. The electrolyte 130 may include a solid state electrolyte (SSE) having a relatively low electric conductivity and a relatively high ionic conductivity.

In an exemplary embodiment, poly(vinylidene fluoride-co-hexafluoropropylene) (PVDF-HFP), polyacrylonitrile (PAN), poly(methylmethacrylate) (PMMA), poly(2-acrylamido-2-methyl-1-propanesulfonic acid) (poly-AMPS) and modified polyethylene oxide (PEO) may be used for a gel-forming polymer for the gel type electrolyte or a polymer for a polymer type electrolyte.

The gel type electrolyte or the polymer type electrolyte may include a lithium salt of a concentration of about 0.1 mol/L to about 1 mol/L. For example, the lithium salt may include lithium bis((trifluoromethypsulfonyl)amide (LiTf$_2$N), lithium trifluoromethanesulfonate (LiTfO) (LiCF$_3$SO$_3$), lithium bis(trifluoromethane)sulfonamide (LiTFSI) or lithium perchlorate (LiClO$_4$). The present disclosure may not be limited to the above materials.

For example, the electrochromic layer 250 including the electrochromic particle 100 and the electrolyte 130 may be formed on the first transparent electrode 230 or the second transparent electrode 240 to have a thickness of about 20 μm to about 200 μm. When the thickness of the electrochromic layer 250 is smaller than about 20 μm, a driving property of the transmittance variable panel 200 may be deteriorated. When the thickness of the electrochromic layer 250 is greater than about 200 μm, the response speed may be reduced and the spread to the adjacent pixel may occur.

The transmittance variable panel 200 may have a transmissive mode or a blocking mode according to application of a voltage. When a voltage is not applied to the first and second transparent electrodes 230 and 240, the transmittance variable panel 200 may transmit a light due to the transparent electrochromic particle 100. When a voltage is applied to first and second transparent electrodes 230 and 240, the shell 120 (of FIGS. 1 and 2) of the electrochromic material of the chemical formulas 1 to 5 may be discolored and the transmittance variable panel 200 may block a light.

The transmittance variable panel 200 may have various transmittances according to application of a voltage, and a visibility and a contrast ratio of a transparent display device may be improved by applying the transmittance variable panel 200 to the transparent display device.

Figure 4:
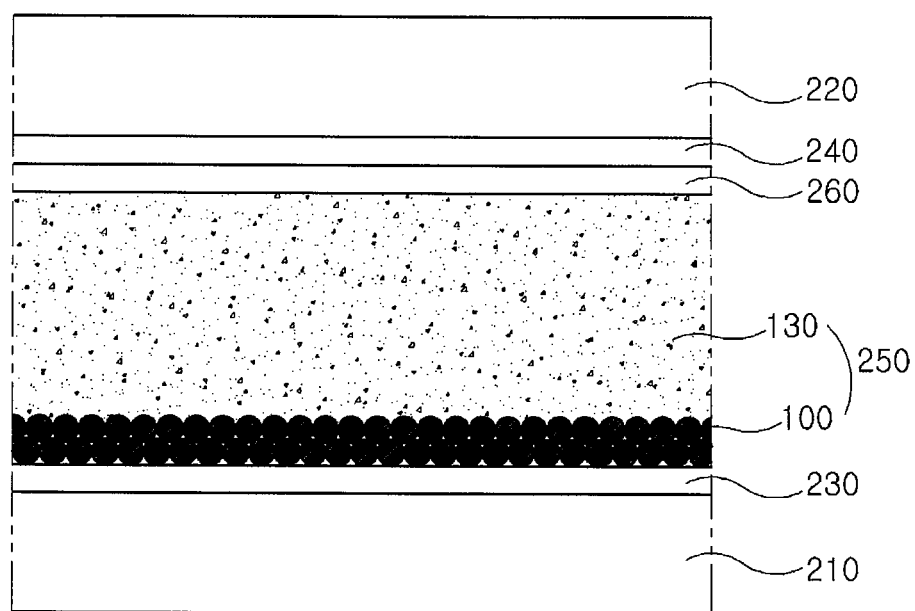
FIG. 4 is a cross-sectional view showing a transmittance variable panel according to a third embodiment of the present disclosure.

FIG. 4 is a cross-sectional view showing a transmittance variable panel according to a third embodiment of the present disclosure.

In FIG. 4, a transmittance variable panel 200' according to a third embodiment of the present disclosure includes first and second substrates 210 and 220 facing into each other, a first transparent electrode 230 on an inner surface of the first substrate 210, a second transparent electrode 240 on an inner surface of the second substrate 220 and an electrochromic layer 250 having an electrochromic particle 100 and a electrolyte 130 between the first and second substrates 210 and 220.

The transmittance variable panel 200' further includes a counter layer 260 between the second transparent electrode 240 and the electrochromic layer 250. The counter layer 260 is used for accelerating an oxidation-reduction reaction due to an electric field in the electrochromic layer 250. For example, the counter layer 260 may include a material selected from a group including poly(3,4-ethylenedioxythiophene) (PEDOT), a metallocene compound such as ferrocene or its derivatives, diphenyl amine, triphenyl amine, phenothiazine polymer and/or phenoxazine polymer. For example, the counter layer 260 may include a metallocene moiety and an acrylic copolymer having triarylamine in Korean Patent Publication No. 10-2016-0053352. In an exemplary embodiment of the present disclosure, the counter layer 260 may have a thickness of about 200 nm to about 800 nm. When the thickness of the counter layer 260 is smaller than about 200 nm, a driving property of the electrochromic layer 250 may be deteriorated. When the thickness of the counter layer 260 is greater than about 800 nm, the response speed may be reduced due to increase of resistance.

The electrochromic layer 250 is disposed between the first and second substrates 210 and 220, i.e., between the first and second transparent electrodes 230 and 240. The electrochromic layer 250 includes the electrochromic particle 100 and the electrolyte 130. The electrochromic particle 100 has a core-shell structure where the electrochromic material of the chemical formulas 1 to 5 wraps the core. The electrochromic material of the chemical formulas 1 to 5 induces a stacking effect by the plurality of bipyridinium salt moieties and the phenyl moiety or the phenoxy moiety where a hydrogen atom is substituted by the electron-rich halogen. As a result, the electrochromic particle 100 has an excellent transmittance when a voltage is not applied. Since the electrochromic particle 100 is a nanoparticle of a spherical shape having a relatively great specific surface area, the electrochromic particle 100 has a prompt discoloration even with a relatively low driving voltage. As a result, when the voltage is applied, the electrochromic particle 100 is promptly discolored to a black to have an excellent light blocking efficiency. The electrochromic material of the chemical formulas 1 to 5 has an excellent infrared (IR) cut effect. Accordingly, when the transmittance variable panel 200' is applied to a smart window for a building or a vehicle, an additional infrared (IR) cut film is not required.

A display device including an electrochromic particle where a shell is formed of an electrochromic material according to the present disclosure will be illustrated hereinafter.

Figure 5:
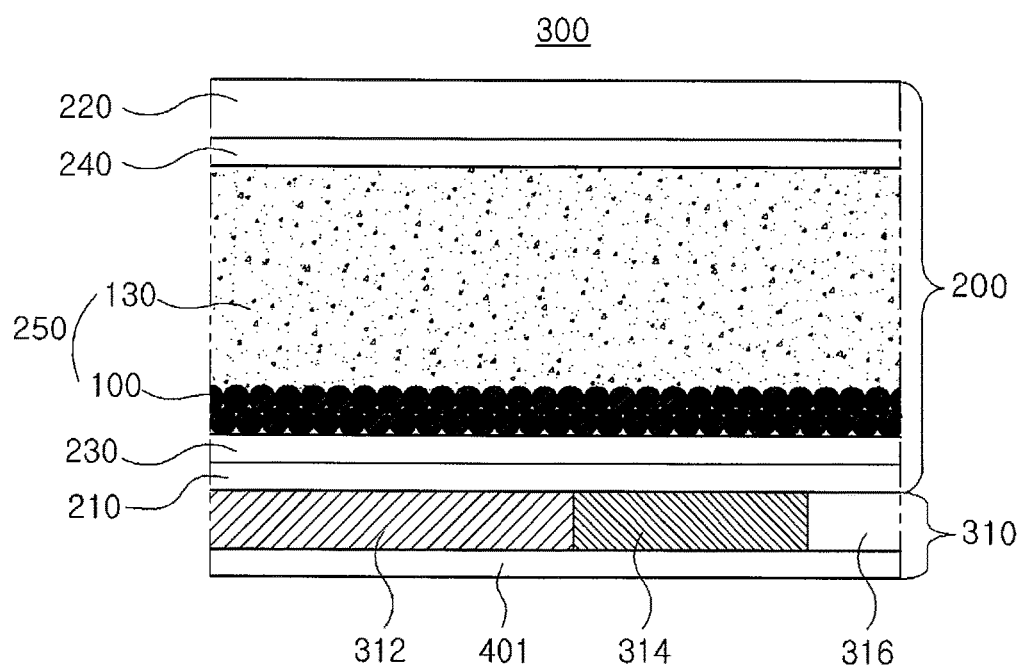
FIG. 5 is a cross-sectional view showing a display device having a transmittance variable panel according to a first embodiment of the present disclosure.
Figure 6:
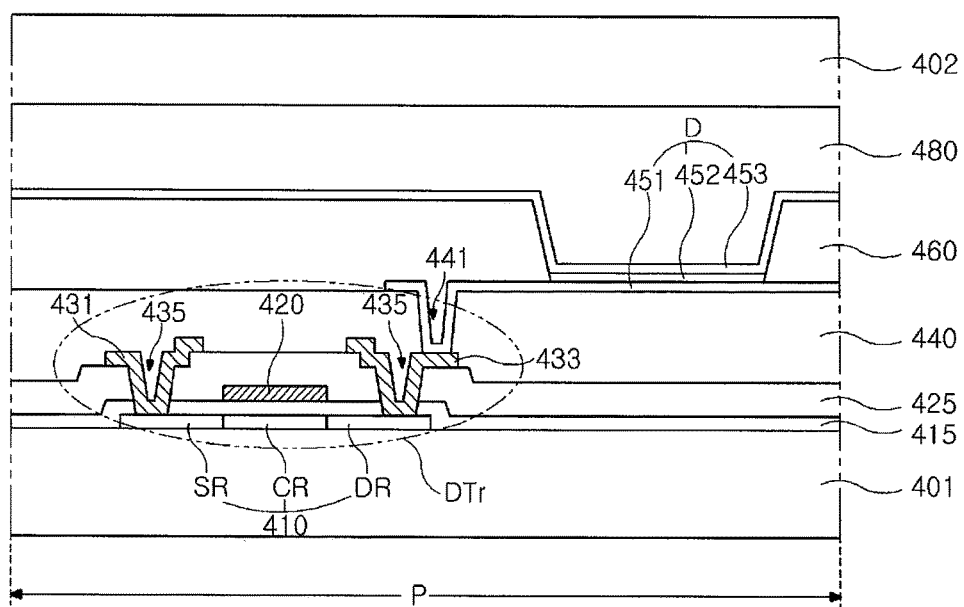
FIG. 6 is a cross-sectional view showing a display panel of a display device having a transmittance variable panel according to a first embodiment of the present disclosure.

FIG. 5 is a cross-sectional view showing a display device having a transmittance variable panel according to a first embodiment of the present disclosure, and FIG. 6 is a cross-sectional view showing a display panel of a display device having a transmittance variable panel according to a first embodiment of the present disclosure.

In FIG. 5, a display device 300 includes a transparent display panel 310 and a transmittance variable panel 200 on the transparent display panel 310. The transparent display panel 310 includes a plurality of pixels, and each of the plurality of pixels includes a display portion 312, a driving portion 314 and a transparent portion 316. The display portion 312 is driven by a voltage or a signal supplied by the driving portion 314 to display an image. The transparent display panel 310 may be a liquid crystal panel or a light emitting diode panel.

The transparent display panel 310 of a light emitting diode panel will be briefly illustrated. In FIG. 6, the transparent display panel 310 includes third and fourth substrates 401 and 402 facing into each other and a light emitting diode D between the third and fourth substrates 401 and 402.

The third and fourth substrates 401 and 402 may include a glass or a plastic. For example, each of the third and fourth substrates 401 and 402 may include polyethylene terephthalate (PET) or polyethylene naphthalate (PEN).

A gate line (not shown), a data line (not shown) and a power line (not shown) are formed on an inner surface of the third substrate 401. The gate line and the data line cross each other to define a pixel P, and the power line may be parallel to the gate line or the data line. Each pixel P includes the display portion 312, the driving portion 314 and the transparent portion 316. A switching thin film transistor (TFT) (not shown) connected to the gate line and the data line is formed in each pixel P.

A driving thin film transistor (TFT) DTr connected to the switching thin film transistor and the power line is formed in each pixel P. The driving TFT DTr includes a semiconductor layer 410, a gate electrode 420, a source electrode 431 and a drain electrode 433. The switching TFT may have a structure similar to the driving TFT DTr.

The semiconductor layer 410 includes a channel region CR, a source region SR and a drain region DR at both sides of the channel region CR. The semiconductor layer 410 may include polycrystalline silicon or an oxide semiconductor material. A buffer layer (not shown) of silicon oxide ($SiO_2$) or silicon nitride (SiNx) may be formed between the semiconductor layer 410 and the third substrate 401.

A gate insulating layer 415 is formed on the semiconductor layer 410. The gate insulating layer may include an inorganic insulating material such as silicon oxide ($SiO_2$) and silicon nitride (SiNx). A gate electrode 420 is formed on the gate insulating layer 415 corresponding to the channel region CR. The gate electrode 420 may include a metallic material such as copper (Cu) and aluminum (Al) having a relatively low resistance.

An interlayer insulating layer 425 is formed on the gate electrode 420. Semiconductor contact holes 435 exposing the source region SR and the drain region DR may be formed in the interlayer insulating layer 425 and the gate insulating layer 415. The interlayer insulating layer 425 may include an inorganic insulating material such as silicon oxide ($SiO_2$) and silicon nitride (SiNx).

A source electrode 431 and a drain electrode 433 are formed on the interlayer insulating layer 425. The source electrode 431 and the drain electrode 433 are connected to the source region SR and the drain region DR, respectively, through the semiconductor contact holes 435. The source electrode 431 and the drain electrode 433 may include the same material as the gate electrode 420.

A passivation layer 440 is formed on the source electrode 431 and the drain electrode 433. The passivation layer 440 may include an inorganic insulating material such as silicon oxide ($SiO_2$) and silicon nitride (SiNx) or an organic insulating material such as photoacryl. A drain contact hole 441 exposing the drain electrode 433 may be formed in the passivation layer 440.

In the first embodiment, the driving TFT DTr includes the semiconductor layer 410 of polycrystalline silicon. In another embodiment, the driving TFT DTr may have an inverted staggered structure including the semiconductor layer of amorphous silicon. In another embodiment, the driving TFT DTr may be an oxide transistor including the semiconductor layer of an oxide semiconductor material. Although not shown, a storage capacitor may be formed in each pixel P.

A light emitting diode D is formed on the passivation layer 440 and is electrically connected to the driving TFT DTr through the drain contact hole 441. The light emitting diode D may include first and second electrodes 451 and 453 and an emitting layer 452 between the first and second electrodes 451 and 453.

The first and second electrodes 451 and 453 may have a transparency. The first and second electrodes 451 and 453 may include a transparent conductive material. For example, the first and second electrodes 451 and 453 may include a transparent conductive material of an oxide type such as indium tin oxide (ITO), indium zinc oxide (IZO), gallium zinc oxide (GZO) and indium gallium zinc oxide (IGZO). One of the first and second electrodes 451 and 453 is an anode, and the other one of the first and second electrodes 451 and 453 is a cathode. The anode may include a material having a relatively great work function, and the cathode may include a material having a relatively low work function. The first electrode 451 is connected to the drain electrode 433 of the driving TFT DTr through the drain contact hole 441 and is patterned by the pixel P. The second electrode 453 is formed to have a single body corresponding to the whole of the pixels P of the display panel 310.

A bank layer 460 is formed on the first electrode 451 and has an opening in each pixel P. The bank layer 460 may divide the adjacent pixels P. The emitting layer 452 is formed in the opening of the bank layer 460 in each pixel P. The emitting layer 452 may emit a light due to combination of a hole and an electron supplied from the first and second electrodes 451 and 453, respectively.

The emitting layer 452 may include an emitting material layer substantially emitting a light. The emitting layer 452 may have a multiple-layered structure to improve an emission efficiency. For example, the emitting layer 452 may further include a hole injecting layer, a hole transporting layer, an electron injecting layer and an electron transporting layer. The light emitting diode D emits a light having a brightness corresponding to a signal applied to the gate electrode 420 of the driving TFT DTr.

The fourth substrate 402 is an encapsulation substrate covering the driving TFT DTr. Although not shown, a barrier layer may be formed between the fourth substrate 402 and the driving TFT DTr to prevent penetration of moisture.

In FIG. 6, a region including driving elements such as the driving TFT DTr corresponds to the driving portion 314 (of FIG. 5), and a region including the light emitting diode D corresponds to the display portion 312 (of FIG. 5). Driving elements and display elements are not formed in the transparent portion 316 (of FIG. 5) and a light passing through the transparent portion 316 (of FIG. 5). The display portion 312 and the driving portion 314 may overlap each other.

In FIG. 5, the transmittance variable panel 200 includes first and second substrates 210 and 220 facing into each other, a first transparent electrode 230 on an inner surface of the first substrate 210, a second transparent electrode 240 on an inner surface of the second substrate 220 and an electrochromic layer 250 having an electrochromic particle 100 and a electrolyte 130 between the first and second substrates 210 and 220. The transmittance variable panel 200 may further include a counter layer 260 (of FIG. 4) between the second transparent electrode 240 and the electrochromic layer 250 for accelerating an oxidation-reduction reaction in the electrochromic layer 250.

The first and second substrates 210 and 220 may include a glass or a plastic. For example, each of the first and second substrates 210 and 220 may include polyethylene terephthalate (PET) or polyethylene naphthalate (PEN).

The first substrate 210 of the transmittance variable panel 200 and the fourth substrate 402 of the display panel 310 are the same as each other in FIGS. 5 and 6. In another embodiment, the first substrate 210 and the fourth substrate 402 may be different from each other, and the transmittance variable panel 200 and the display panel 310 may be attached to each other. The first and second transparent electrodes 230 and 240 may include a transparent conductive material.

The electrochromic layer 250 is disposed between the first and second transparent electrodes 230 and 240. The electrochromic layer 250 includes the electrochromic particle 100 and the electrolyte 130. The electrochromic particle 100 has a core-shell structure where the shell of the electrochromic material of the chemical formulas 1 to 5 wraps the core. The electrochromic material of the chemical formulas 1 to 5 induces a stacking effect by the plurality of bipyridinium salt moieties and the phenyl moiety or the phenoxy moiety where a hydrogen atom is substituted by the electron-rich halogen. As a result, the electrochromic particle 100 has an excellent transmittance when a voltage is not applied. In addition, since the electrochromic particle 100 is a nanoparticle of a spherical shape having a relatively great specific surface area, the electrochromic particle 100 has a prompt discoloration even with a relatively low driving voltage. As a result, when the voltage is applied, the electrochromic particle 100 is promptly discolored to a black to have an excellent light blocking efficiency. The electrochromic material of the chemical formulas 1 to 5 has an excellent infrared (IR) cut effect. Accordingly, when the transmittance variable panel 200 is applied to a smart window for a building or a vehicle, an additional infrared (IR) cut film is not required.

A gel type electrolyte or a polymer type electrolyte including a dissolved lithium salt may be used for the electrolyte 130 of the electrochromic layer 250. The medium of the electrolyte 130 may be cured by a heat or a light. The electrolyte 130 may include a solid state electrolyte (SSE) having a relatively low electric conductivity and a relatively high ionic conductivity.

The transmittance variable panel 200 may have a transmissive mode or a blocking mode according to application of a voltage. When a voltage is not applied to the first and second transparent electrodes 230 and 240, the transmittance variable panel 200 may transmit a light due to the transparent electrochromic particle 100. When a voltage is applied to first and second transparent electrodes 230 and 240, the shell 120 (of FIGS. 1 and 2) of the electrochromic material of the chemical formulas 1 to 5 may be discolored and the transmittance variable panel 200 may block a light.

When a voltage is not applied to the first and second transparent electrodes 230 and 240, the shell 120 of the electrochromic particle 100 has a transparent mode, and the transmissive variable panel 200 has a transmissive mode to transmit a light of the transparent portion 316. When a voltage is applied to the first and second transparent electrodes 230 and 240, the shell 120 of the electrochromic particle 100 is discolored to a black, and the transmissive variable panel 200 has a blocking mode to block a light of the transparent portion 316. As a result, the display device 300 including the transmittance variable panel 200 is used as a transparent display device.

In the electrochromic material of the chemical formulas 1 to 5, a plurality of bipyridinium salt moieties are combined to a benzene ring, and a phenyl moiety or a phenoxy moiety where a hydrogen atom is substituted by an electron-rich halogen may induce a stacking effect with the plurality of bipyridinium salt moieties. Since the electrochromic particle 100 of a structure where the electrochromic material wraps the core 110 has an excellent transparency, a transmittance increases when an electric field is not applied. Since the shell 120 of the electrochromic material is discolored into a black even by a relatively low driving voltage, a light blocking efficiency is improved. In addition, since the electrochromic material of the present disclosure is discolored into a black by application of a voltage, the electrochromic material has an excellent light blocking efficiency without mixing of other materials. Accordingly, a visibility and a contrast ratio of a transparent display device are improved. In addition, since the shell and the core are chemically combined with each other, a driving stability of the transparent display device is improved. Further, since the electrochromic material of the chemical formulas 1 to 5 has an excellent infrared (IR) cut effect, an additional infrared (IR) cut film is not required when the transmittance variable panel 200 is applied to a smart window for a building or a vehicle.

The present disclosure will be illustrated with exemplary embodiments. However, the present disclosure may not be limited to the following embodiments.

SYNTHESIS EXAMPLE 1

Composition of Electrochromic Material (Shutter Shell Material)

An electrochromic material of the chemical formula 2 where X is bis((trifluoromethyl)sulfonyl)imide negative ion $((CF_3SO_2)_2N^-)$ was synthesized. In a 3 necks flask of a nitrogen atmosphere, 15.6 g of 4,4'-bipyridine (0.1 mol) and 24.5 g of bromoethyl phosphonic acid (0.1 mol) were added to a solution where methanol and a water were mixed with 50:50, and the solution was refluxed at a temperature of about 80° C. for 12 hours. Next, the solvent was distilled and purified to obtain a solid of a white. 40.0 g of the white solid and 35.6 g of 1,2,4,5-tetrabromo benzene (0.1 mol) were added to a solvent where ethanol and toluene were mixed with 80:20, and the solution was reacted for 3 days. Subsequently, 0.1 mol of 2,2'-bipyridine-6-carboxylic acid was added to the solution, and the solution was reacted for 2 days. Next, a material of a light yellow is obtained through purification.

Figure 7:
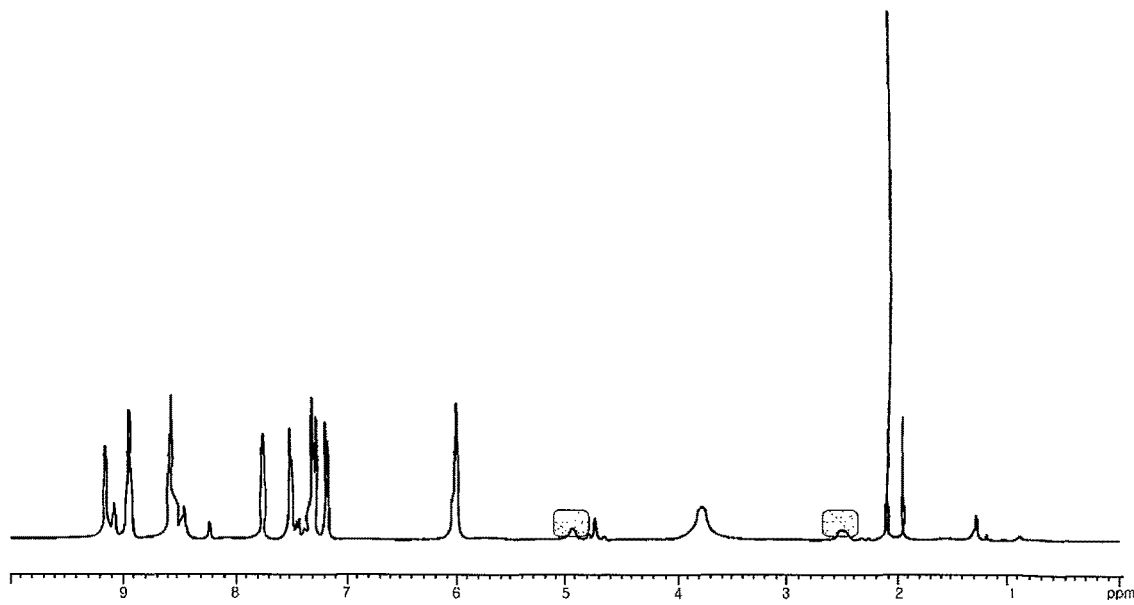
FIG. 7 is a graph showing a result of a nuclear magnetic resonance (NMR) measurement with respect to an electrochromic material synthesized according to a synthesis example 1.

70 g of the obtained material of a light yellow was added to 7.1 g of 3-oxo-3-(4-phenoxy phenyl)propionic acid methyl ester (0.026 mol), 5.2 g of 1-bromo-3-trifluoromethoxy benzene, 31.2 g of bipyridine (0.2 mol) and 300 g of methanol, and the solution was reacted at a temperature of about 80° C. for 12 hours. Next, the solution was firstly treated with hydrochloride (HCl) solution (38wt %) and an impurity except for a target compound was removed through recrystallization to obtain a compound of an ivory. Next, in 1 L flask, the obtained compound was added to 1-ethyl-3methyl-imidazolium-bis-trifluoromethyl sulfonyl imide. An ion exchange was performed to the solution and the electrochromic material of the chemical formula 2 was synthesized through recrystallization of the solution. The result of nuclear magnetic resonance (NMR) measurement with respect to the electrochromic material synthesized according to synthesis example 1 was shown in FIG. 7.

SYNTHESIS EXAMPLE 2

Composition of Electrochromic Material (Shutter Shell Material)

An electrochromic material of the chemical formula 3 where X is bis((trifluoromethyl)sulfonyl)imide negative ion $((CF_3SO_2)_2N^-)$ was synthesized. The process of synthesis example 1 except that 2,2'-bipiridine-6-ethyl-phosphoric acid was used instead of 2,2'-bipyridine-6-carboxylic acid and 1-bromohexane was used instead of 3-oxo-3-(4-phenoxy phenyl)propionic acid methyl ester was repeated to obtain the electrochromic material of the chemical formula 3.

SYNTHESIS EXAMPLE 3

Composition of Electrochromic Material (Shutter Shell Material)

An electrochromic material of the chemical formula 4 where X is bis((trifluoromethyl)sulfonyl)imide negative ion $((CF_3SO_2)_2N^-)$ was synthesized. The process of synthesis example 1 except that 2,2'-bipiridine-6-ethyl-phosphoric acid was used instead of 2,2'-bipyridine-6-carboxylic acid and 4-aminobenzyl alcohol was used instead of 3-oxo-3-(4-phenoxy phenyl)propionic acid methyl ester was repeated to obtain the electrochromic material of the chemical formula 4.

SYNTHESIS EXAMPLE 4

Composition of Electrochromic Material (Shutter Shell Material)

An electrochromic material of the chemical formula 5 where X is bis((trifluoromethyl)sulfonyl)imide negative ion $((CF_3SO_2)_2N^-)$ was synthesized. The process of synthesis example 1 except that 2,2'-bipiridine-6-ethyl-phosphoric acid was used instead of 2,2'-bipyridine-6-carboxylic acid and benzyl bromide was used instead of 3-oxo-3-(4-phenoxy phenyl)propionic acid methyl ester was repeated to obtain the electrochromic material of the chemical formula 5.

COMPARISON SYNTHESIS EXAMPLE 1

Composition of Electrochromic Material (Shutter Shell Material)

The electrochromic material represented by a following chemical formula 6 was synthesized.

Chemical Formula 6

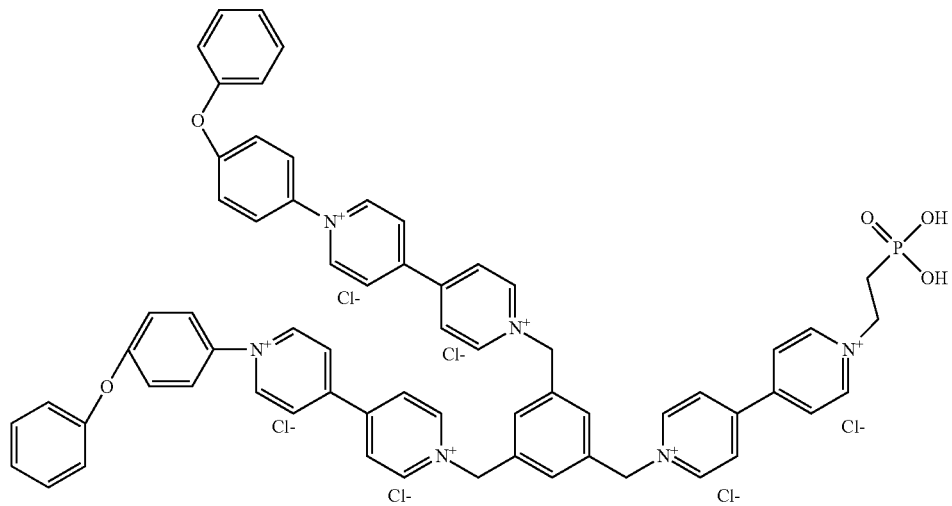

In a 3 necks flask of a nitrogen atmosphere, 15.6 g of bipyridine (0.1 mol) and 24.5 g of bromoethyl phosphonic acid (0.1 mol) were added to a solution of methanol and water (50:50), and the solution was refluxed at a temperature of about 80° C. for 12 hours. Next, the solvent was distilled and purified to obtain a white solid. 40.0 g of the white solid and 35.6 g of 1,3,5-tribromo benzene (0.1 mol) were added to a solvent of ethanol and toluene (80:20), and the solution was reacted for 3 days. Next, a material of a light yellow was obtained through purification. 70 g of the obtained material of a light yellow was added to 7.1 g of 3-oxo-3-(4-phenoxy phenyl)propionic acid methyl ester (0.026 mol), 31.2 g of bipyridine (0.2 mol) and 300 g of methanol, and the solution was reacted at a temperature of about 80° C. for 12 hours. Next, the solution was firstly treated with hydrochloride (HCl) solution (38 wt %) and an impurity except for a target compound was removed through recrystallization to obtain a compound of the chemical formula 6.

SYNTHESIS EXAMPLE 5

Composition of Electrochromic Particle

After 2.0 g of the electrochromic material synthesized in the synthesis example 1 was dissolved in 20 g of methanol, the solution was stirred using an ultrasonic wave at a temperature of about 50° C. for 3 hours to obtain a transparent solution. In a 250 mL wide mouth bottle, 50 g of an indium tin oxide (ITO) powder (first particle size >15 nm, Solvay GmbH), 0.5 g of 2,4-pentanedion and 0.05 g of non-aqueous organic binder BYK160 were added to 120 g of isopropyl alcohol and the solution was stirred for 1 hour. 200 g of zirconia bead having a diameter of 1.0 mm was added to 50 g of the transparent solution and the solution was sealed. Next, the zirconia bead was dispersed for 24 hours using a ball mill moving with 600 rpm to obtain an electrochromic particle solution (a solution where an electrochromic particle is dispersed).

SYNTHESIS EXAMPLES 6-8

Composition of Electrochromic Particle

The process of the synthesis example 5 except that the electrochromic materials synthesized in the synthesis examples 2 to 4 were used instead of the electrochromic material synthesized in the synthesis example 1 was repeated to obtain electrochromic particle solutions.

COMPARISON SYNTHESIS EXAMPLE 2

Composition of Electrochromic Particle

The process of the synthesis example 5 except that the electrochromic materials synthesized in the comparison synthesis example 1 was used instead of the electrochromic material synthesized in the synthesis example 1 was repeated to obtain an electrochromic particle solution.

EXAMPLE 1

Fabrication of Unit Cell of Transmittance Variable Panel

A unit cell was fabricated using the electrochromic particle solution synthesized in the synthesis example 5. The solid electrolyte was fabricated through a following method. In a flask having a stirrer, 300 g of acetonitrile, 10.0 g of polyethylene oxide (molecular weight 600K) and 15.0 g of siloxane where 0.8 mol of ethylene oxide were added and stirred for 60 minutes. 1.77 g of lithium bis-trifluoromethane sulfon imide (LiTFSI), 0.5 g of S104 (Air Product Inc.) as an additive and 0.05 g of OXE01 (BASF Corp.) as a photoinitiator were added to the solution and the solution was stirred at a temperature of 50° C. for 6 hours to obtain a transparent electrolyte solution. After the solid electrolyte was coated on electrodes separated by a gap of 1 mm, the solvent was dried. An impedance was measured by irradiating an ultraviolet (UV) ray of 0.1 J/cm$^2$. An ionic conductivity of the solid electrolyte layer was 5.4×10$^{-5}$ S/cm.

In addition, the counter layer was formed through a following method. In a flask having a stirrer, 30 g of vinyl ferrocene and 300 g of chlorobenzene were added and stirred for melting. After a temperature increases to 60° C., an initiator for a radical polymerization was added with a speed of 0.05 g/min and the solution was reacted for 23 hours to obtain a vinyl ferrocene polymer having a molecular weight of 8000. The polymer was melted in dichlorobenzene and the counter layer was formed on a double-sided indium tin oxide (ITO) glass having a sheet resistance of 40 Ω/sq by a spin coating of 1000 rpm of the solution.

Next, the electrochromic particle solution obtained from the synthesis example 5 was coated on an indium tin oxide (ITO) glass having a sheet resistance of 40 Ω/sq to form a film having a thickness of 4 μm, and the electrochromic particle layer was dried at a temperature of 80° C. for 30 minutes. Next, an electrolyte of an ultraviolet (UV) cure type was coated on the electrochromic particle layer, and the electrolyte layer is cured by irradiating a UV ray of 0.1 J/cm$^2$ to form a solid electrolyte layer having a thickness of 100 μm.

Next, the ITO glass having the electrochromic particle layer and the solid electrolyte layer was attached to the double-sided ITO glass having the counter layer at a temperature of 40° C. to form the unit cell of the transmittance variable panel having an active region of 100 mm×100 mm.

EXAMPLES 2-4

Fabrication of Unit Cell of Transmittance Variable Panel

The process of the example 1 except that the electrochromic particle solution in the synthesis examples 6 to 8 was used instead of the electrochromic particle solution in the synthesis example 5 was repeated to obtain transmittance variable panels.

EXAMPLE 5

Fabrication of Unit Cell of Transmittance Variable Panel

The process of the example 1 except that an electrode having the copper (Cu) mesh (sheet resistance of 1 Ω/sq) and an ITO layer (sheet resistance of 40 Ω/sq) was used instead of the ITO electrode was repeated to obtain transmittance variable panels.

COMPARISON EXAMPLE 1

Fabrication of Unit Cell of Transmittance Variable Panel

The process of the example 1 except that the electrochromic particle solution in the comparison synthesis example 2 was used instead of the electrochromic particle solution in the synthesis example 5 was repeated to obtain a transmittance variable panel.

COMPARISON EXAMPLE 2

Fabrication of Unit Cell of Transmittance Variable Panel

The process of the example 1 except that tungsten oxide (WO$_3$) as the electrochromic particle was used instead of the electrochromic particle solution in the synthesis example 5 was repeated to obtain a transmittance variable panel.

EXPERIMENT EXAMPLE

Measurement of Physical Property of Transmittance Variable Panel

A transmittance, a response speed and a driving voltage were measured with respect to the transmittance variable panels fabricated in the examples 1 to 4 and the comparison examples 1 and 2. An aging process where +1.3V and −1.3V are applied was repeated to the transmittance variable panels by 50 times with an interval of 10 sec. Next, the transmittance of ON(black)/OFF(white, transparent) states was measured in a visible band using DMS803 (spectrophotometer of Konica Minolta Inc.), and the transmittance of ON/OFF states was measured in an infrared (IR) band using FT-IR spectrometer.

Figure 8:
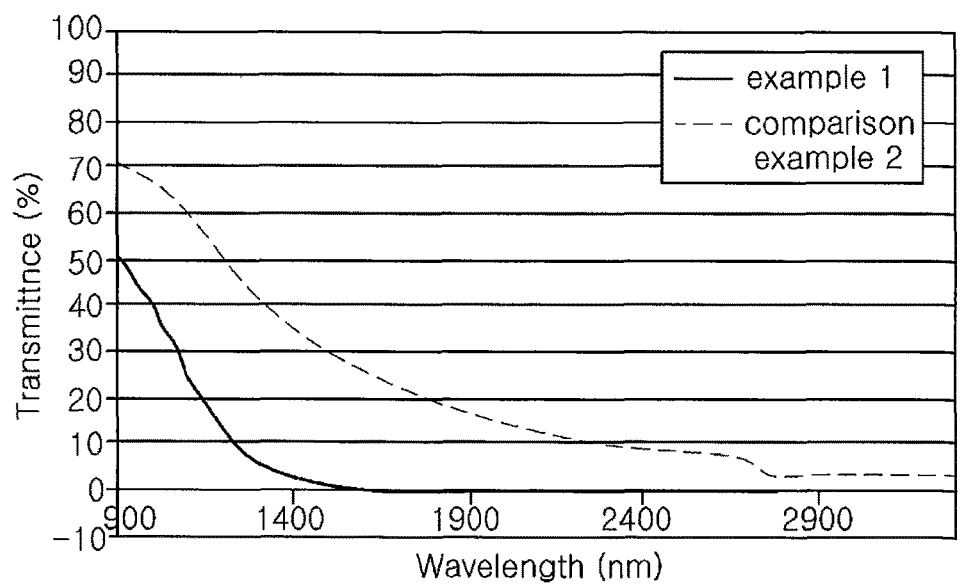
FIG. 8 is a graph showing a transmittance of transmittance variable panels of examples and comparison examples with respect to a wavelength corresponding to an infrared ray.

TABLE 1 shows a transmittance of a wavelength band of visible ray (380 nm to 780 nm), a response speed and a driving voltage of transmittance variable panels of examples and comparison examples, and TABLE 2 shows a driving start voltage, a driving end voltage and a gray level of transmittance variable panels of examples and comparison examples. FIG. 8 is a graph showing a transmittance of transmittance variable panels of examples and comparison examples with respect to a wavelength corresponding to an infrared ray, and FIG. 9 is a graph showing a transmittance of transmittance variable panels of examples and comparison examples with respect a driving voltage.

Figure 9:
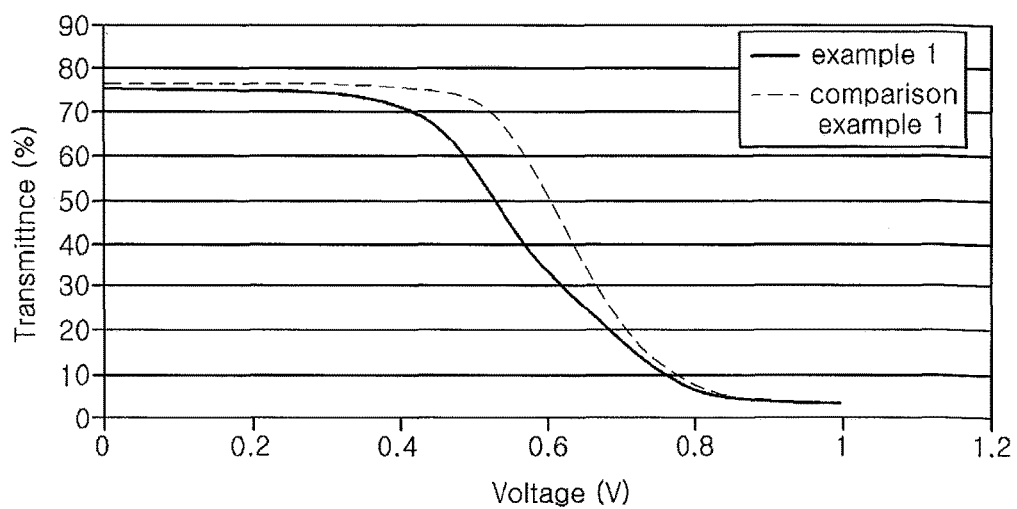
FIG. 9 is a graph showing a transmittance of transmittance variable panels of examples and comparison examples with respect a driving voltage.

In TABLEs 1 and 2 and FIGS. 8 and 9, the transmittance variable panel including the electrochromic particle where the shell includes the electrochromic material of the present disclosure has OFF and ON states. The transmittance of the OFF state is improved, and the blocking rate of the ON state is improved.

TABLE 1

|  | transmittance (off state) | transmittance (on state) | response speed (T90) | driving voltage (V) |
|---|---|---|---|---|
| example 1 | 75% | 1.9% | ~9 sec | 0.90 |
| example 2 | 75% | 1.9% | ~9 sec | 0.91 |
| example 3 | 75% | 1.9% | ~9 sec | 0.93 |
| example 4 | 75% | 1.9% | ~9 sec | 0.91 |
| example 5 | 71% | 1.9% | ~1 sec | 0.90 |
| comparison example 1 | 75% | 2.2% | ~9 sec | 1.0 |
| comparison example 2 | 65% | 20% | ~90 sec | 2.2 |

TABLE 2

|  | Start voltage | End voltage | Gray Level |
|---|---|---|---|
| example 1 | 0.38 V | 0.84 V | 16 |
| example 2 | 0.40 V | 0.83 V | 16 |

TABLE 2-continued

|  | Start voltage | End voltage | Gray Level |
|---|---|---|---|
| example 3 | 0.37 V | 0.79 V | 16 |
| example 4 | 0.40 V | 0.88 V | 16 |
| example 5 | 0.38 V | 0.84 V | 16 |
| comparison example 1 | 0.52 V | 0.86 V | 10 |

Consequently, since a phenyl moiety or a phenoxy moiety where a hydrogen atom is substituted by an electron-rich halogen and a bipyridinium salts moiety connected as a linker cause a stacking effect, an electrochromic material of the present disclosure has an excellent transmittance in an OFF state and an excellent blocking efficiency in an ON state. As a result, a transmittance variable panel including an electrochromic particle of a core and a shell of an electrochromic material has an excellent transmittance and an excellent blocking efficiency.

Specifically, since the electrochromic particle of the present disclosure is an exemplary spherical nanoparticle, a specific surface area of the electrochromic particle increases and the blocking efficiency of the transmittance variable panel increases.

In addition, when the electrochromic particle where the electrochromic material of the present disclosure is used as the shell is applied to the transmittance variable panel, a response speed increases and a prompt discoloration is obtained. Since the electrochromic particle has a state where the core and the shell are chemically combined to each other, a driving stability is improved due to the stacking effect and the discoloration is obtained even with a relatively low driving voltage.

Further, since the transmittance variable panel of the present disclosure is fabricated as a film type by using a solid phase electrolyte, a leakage of a fluid is prevented and the transmittance variable panel of a thin profile is obtained.

Moreover, since a display device including the transmittance variable panel of the present disclosure has an excellent transmittance, a visibility and a contrast ratio are improved.

Furthermore, since the electrochromic material of the present disclosure has a function of an infrared (IR) cut, the transmittance variable panel is applied to a window or a smart window for a vehicle without an additional IR cut film.

A number of examples have been described above. Nevertheless, it will be understood that various modifications may be made. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. An electrochromic material represented by a following chemical formula 1,

Chemical Formula 1

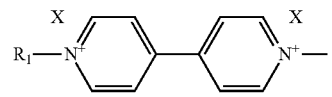

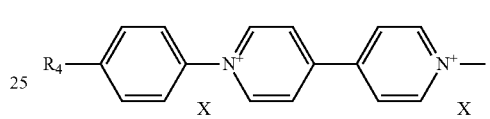

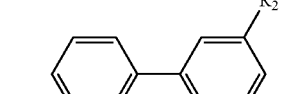

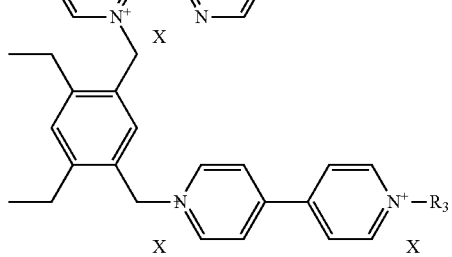

wherein,

R1 is a hydrogen atom, an alkyl group of C1 to C30, an alkenyl of C2 to C30, an alkynyl group of C2 to C30, an alkoxy group of C1 to C30, a cycloalkyl group of C4 to C30, a heterocycloalkyl group of C4 to C30, an aryl group of C5 to C30, a heteroaryl group of C5 to C30, an aralkyl group of C5 to C30, an heteroaralkyl group of C5 to C30, an aryloxy group of C5 to C30 or an heteroaryloxy group of C5 to C30;

each of R2 and R3 is —W—Z, wherein Z is independently selected from a group including a carboxylic acid (—COOH), a sulfonic acid (—SO$_3$H$_2$), a boronic acid (B(OH)$_2$), a phosphoric acid (PO$_3$H$_2$) and a phosphinic acid (PO$_2$H$_2$), and W is a direct bond or an alkylene group of C1 to C20;

R4 is an alkyl group of C1 to C10 substituted by one or more halogens or an alkoxy group of C1 to C10 substituted by one or more halogens; and X is a halogen negative ion, PF$_6^-$, BF$_4^-$, BH$_4^-$, ClO$_4^-$, CF$_3$SO$_3^-$ or (CF$_3$SO$_2$)$_2$N$^-$.

2. The electrochromic material of claim 1, wherein the electrochromic material is represented by one of following chemical formulas 2 to 5,

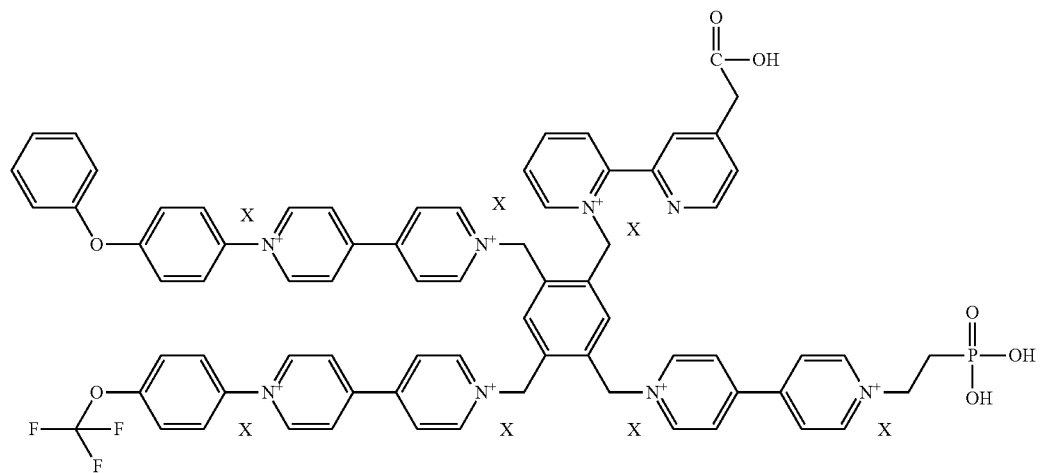
Chemical Formula 2
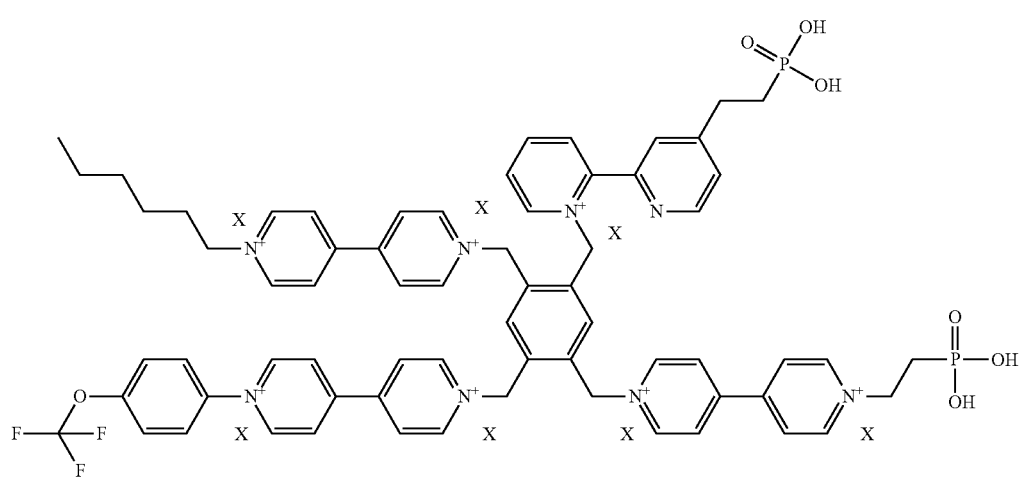
Chemical Formula 3
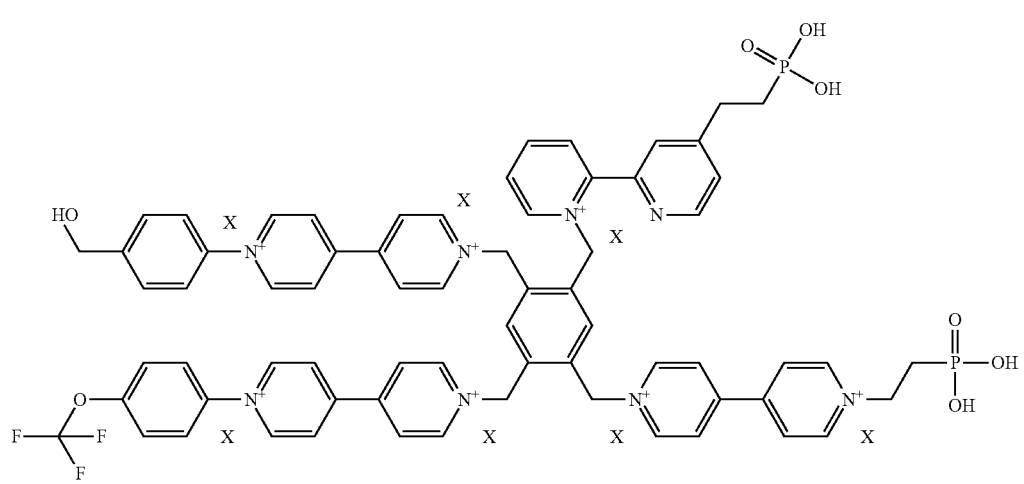
Chemical Formula 4

-continued

Chemical Formula 5

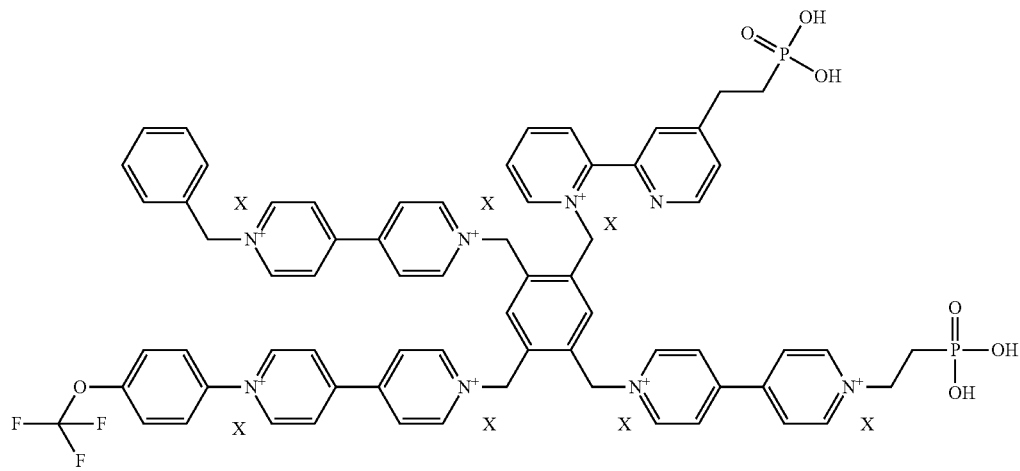

wherein X is defined the same as that in the chemical formula 1.

3. An electrochromic particle comprising:
a core; and
a shell wrapping the core,
wherein the shell includes the electrochromic material of claim 1.

4. An electrochromic particle of claim 3 wherein the shell includes the electrochromic material of claim 2.

5. The electrochromic particle of claim 3, wherein the core is selected from a group including a conductive metal oxide, a non-conductive metal oxide and a combination thereof,
wherein the conductive metal oxide is selected from a group including indium tin oxide (ITO), indium zinc oxide (IZO), antimony tin oxide (ATO), fluorine-doped tin oxide (FTO), aluminum zinc oxide (AZO) and a combination thereof, and
wherein the non-conductive metal oxide is selected from a group including titanium oxide ($TiO_2$), silica ($SiO_2$), zinc oxide (ZnO), zirconia ($ZrO_2$) and a combination thereof.

6. The electrochromic particle of claim 3, wherein the core includes a first core and a second core wrapping the first core,
wherein the first core is selected from a group including indium tin oxide (ITO), indium zinc oxide (IZO), antimony tin oxide (ATO), fluorine-doped tin oxide (FTO), aluminum zinc oxide (AZO) and a combination thereof, and
wherein the second core is selected from a group including titanium oxide ($TiO_2$), silica ($SiO_2$), zinc oxide (ZnO), zirconia ($ZrO_2$) and a combination thereof.

7. The electrochromic particle of claim 4, wherein the core is selected from a group including a conductive metal oxide, a non-conductive metal oxide and a combination thereof,
wherein the conductive metal oxide is selected from a group including indium tin oxide (ITO), indium zinc oxide (IZO), antimony tin oxide (ATO), fluorine-doped tin oxide (FTO), aluminum zinc oxide (AZO) and a combination thereof, and
wherein the non-conductive metal oxide is selected from a group including titanium oxide ($TiO_2$), silica ($SiO_2$), zinc oxide (ZnO), zirconia ($ZrO_2$) and a combination thereof.

8. The electrochromic particle of claim 4, wherein the core includes a first core and a second core wrapping the first core,
wherein the first core is selected from a group including indium tin oxide (ITO), indium zinc oxide (IZO), antimony tin oxide (ATO), fluorine-doped tin oxide (FTO), aluminum zinc oxide (AZO) and a combination thereof, and
wherein the second core is selected from a group including titanium oxide ($TiO_2$), silica ($SiO_2$), zinc oxide (ZnO), zirconia ($ZrO_2$) and a combination thereof.

9. A transmittance variable panel comprising:
first and second substrates facing into each other;
a first transparent electrode on an inner surface of the first substrate;
a second transparent electrode on an inner surface of the second substrate; and
an electrochromic layer between the first and second transparent electrodes, the electrochromic layer including an electrochromic particle of claim 3.

10. The transmittance variable panel of claim 9, further comprising a counter layer between the second transparent electrode and the electrochromic layer, wherein the counter layer accelerates an oxidation-reduction reaction in the electrochromic layer.

11. A display device comprising:
a transmittance variable panel of claim 9; and
a display panel under the transmittance variable panel, the display panel including a display portion and a transparent portion.

* * * * *

UNITED STATES PATENT AND TRADEMARK OFFICE
CERTIFICATE OF CORRECTION

PATENT NO. : 10,196,561 B2
APPLICATION NO. : 15/623007
DATED : February 5, 2019
INVENTOR(S) : June-Hwan Kim et al.

Page 1 of 2

It is certified that error appears in the above-identified patent and that said Letters Patent is hereby corrected as shown below:

In the Specification

Column 6 Chemical Formula 4:

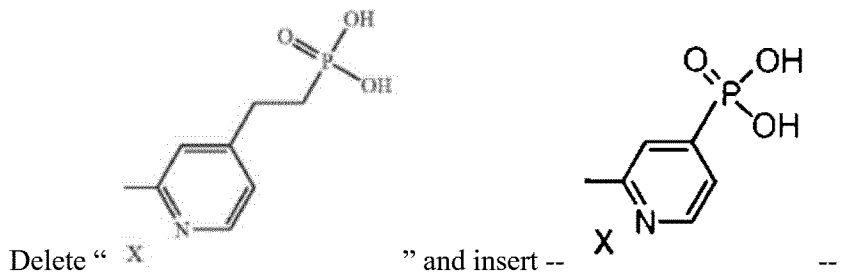

Column 12 Chemical Formula 4:

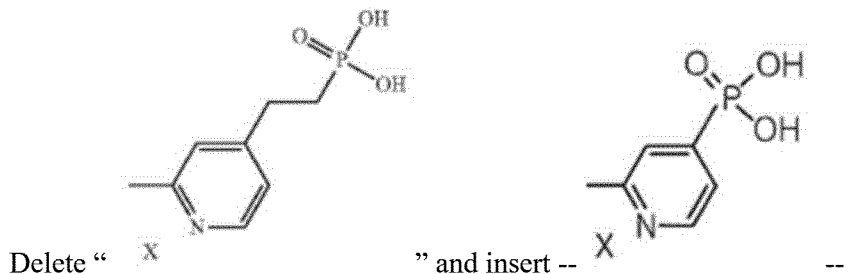

Signed and Sealed this
Twenty-third Day of June, 2020

Andrei Iancu
*Director of the United States Patent and Trademark Office*

CERTIFICATE OF CORRECTION (continued)
U.S. Pat. No. 10,196,561 B2

In the Claims

Column 30, Claim 2 Chemical Formula 4:

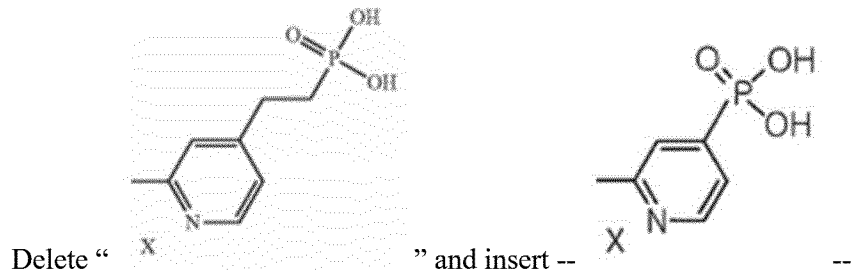

Delete " " and insert -- --